United States Patent
Cuzzato et al.

(12) 
(10) Patent No.: US 6,512,150 B1
(45) Date of Patent: Jan. 28, 2003

(54) PROCESS FOR PURIFYING PENTAFLUOROETHANE FROM CHLOROPENTAFLUOROETHANE

(75) Inventors: Paolo Cuzzato, Treviso (IT); Sergio Peron, Venezia (IT)

(73) Assignee: Ausimont S.p.A., Milan (IT)

( * ) Notice: Subject to any disclaimer, the term of this patent is extended or adjusted under 35 U.S.C. 154(b) by 0 days.

(21) Appl. No.: 09/618,116

(22) Filed: Jul. 17, 2000

(30) Foreign Application Priority Data

Jul. 20, 1999 (IT) .......................................... MI99A1596

(51) Int. Cl.$^7$ ............................................... C07C 17/38
(52) U.S. Cl. ........................................................ 570/177
(58) Field of Search .......................................... 570/177

(56) References Cited

U.S. PATENT DOCUMENTS

| | | |
|---|---|---|
| 5,345,014 A | 9/1994 | Cuzzato |
| 5,346,595 A | 9/1994 | Clemmer et al. |
| 5,841,006 A | 11/1998 | Cuzzato |

FOREIGN PATENT DOCUMENTS

| | | |
|---|---|---|
| EP | 0 356 892 A1 | 3/1990 |
| EP | 0 508 631 A1 | 10/1992 |
| EP | 0 537 760 A2 | 4/1993 |
| EP | 0 612 709 A1 | 8/1994 |
| EP | 0 687 660 A1 | 12/1995 |
| FR | 1383927 | 11/1963 |
| WO | WO 95/16654 | 6/1995 |

OTHER PUBLICATIONS

"Methods for Separating Chloro–carbons from Hydrofluoroalkanes"; 2244 Research Disclosure (1994) Apr., No. 360, Emsworth, GB.

*Primary Examiner*—Alan Siegel
(74) *Attorney, Agent, or Firm*—Arent Fox Kintner Plotkin & Kahn PLLC

(57) ABSTRACT

A gaseous process for reducing the amount of chloropentafluoroethane (CFC 115) impurity present in pentafluoroethane (HFC 125) characterized in that pentafluroethane is allowed to flow on a catalyst formed by a trivalent chromium salt, optionally supported, at temperatures in the range 200° C.–400° C., obtaining the reaction of chloropentafluoroethane with pentafluoroethane with formation of hexafluoroethane (FC 116) and tetrafluorochloroethane (HCFC 124).

9 Claims, No Drawings

PROCESS FOR PURIFYING PENTAFLUOROETHANE FROM CHLOROPENTAFLUOROETHANE

The present invention relates to a process for purifying pentafluoroethane HFC-125 from chloropentafluoroethane CFC 115.

CFC 115 is an impurity of HFC-125 which forms in the processes for the production of pentafluoroethane. Besides, it is an impurity very difficult to be separated from HFC-125 by distillation.

It is possible to directly obtain by synthesis, according to the processes of the prior art, HFC 125 having high purity but with yield damage and therefore decreasing the profitability of these processes.

HFC 125 is industrially produced by direct fluorination of perchloroethylene or of a halogenated compound of general formula $C_2HX_5$, wherein X is any combination of halogens of which at least one different from fluorine, or by dismutation of HCFC 124 (tetrafluorochloroethane $C_2HF_4Cl$) to HFC 125 and HCFC-123.

The former route is more direct than the latter, but it has a lower selectivity. When the reaction conditions are forced towards the production of HFC 125, significant amounts of CFC 115 are formed, or, when the reaction is carried out so as to favour the selectivity, the amounts of pentafluoroethane obtained from the reaction are insufficient to make the process industrially profitable. Besides in the fluorination process it is necessary to use HCFC 124 having an high purity, free from CFC 114 which in the fluorination reaction would lead to the formation of CFC 115, as reported in WO 95/16,654. Therefore the purification of HCFC 124 in the fluorination process is an additional cost of said process.

Also in the process for obtaining pentafluoroethane by dismutation of HCFC 124, obtained by fluorinating the above mentioned halogenated compounds followed by purification to remove CFC 114, it is not possible to obtain high conversions, since CFC 115 forms together with other by-products, although in lower amounts with respect to the direct fluorination process. See U.S. Pat. No. 5,841,006 in the name of the Applicant.

In conclusion the obtainment of very pure HFC 125 by direct synthesis according to the prior art processes has the drawback to decrease the process yields and/or increase the production costs due to the purification step of the intermediate compounds.

Alternatively, it is possible to use processes allowing the purification of HFC 125 from CFC 115. In EP 687,660 a process is described for purifying HFC 125 by reacting with hydrogen a mixture formed by at least 85% by volume of pentafluoroethane and of chloropentafluoroethane in % by volume not higher than 15%, in the presence of a group VIII metal catalyst, at temperatures in the range 170° C.–400° C. As known the reactions wherein gaseous hydrogen is used require a specific plant, since this gas is flammable and explosive and besides it is incompatible with various metal materials. In EP 508,631 a reduction process of CFC 115 by its absorption in an organic solution of a complex metal hydride is described. The use of these reactants implies high costs. Besides, hydrides in the presence of traces of moisture develop hydrogen, wherefore also in this case it is valid what said for the process of EP 687,660. In U.S. Pat. No. 5,346,595 a multistage distillation process is described to remove CFC 115 from HFC 125. The process requires a separate distillation section and at least two distinct distillation steps, working at different pressures, with optional recycle in the second step. The maximum obtainable purity of HFC 125 is 99.8% with 0.2% of residual content of CFC 115, therefore still very high.

The need was therefore felt of a simplified process for purifying HFC 125 from CFC 115, economically cheaper than those of the prior art, in particular such as not to require a specific plant HF or hydrogen resistant.

The present invention is related to the solution of this technical problem.

It is an object of the present invention a gaseous process for substantially reducing the amount of chloropentafluoroethane (CFC 115) impurity present in pentafluoroethane (HFC 125) characterized in that pentafluoroethane is allowed to flow on a fluorination catalyst in solid phase, optionally supported, at temperatures in the range 200° C.–400° C., preferably 280° C.–350° C., obtaining the reaction of chloropentafluoroethane with pentafluoroethane with formation of hexafluoroethane (FC 116) and tetrafluorochloroethane (HCFC 124).

Both FC 116 and HCFC 124 are easily separable from HFC 125; besides HCFC 124 can be recycled in the synthesis process of HFC 125. FC 116 is an industrially useful product. The process according to the present invention does not require the addition of reactants converting CFC 115 into an easily separable product from HFC 125.

The trivalent chromium salt catalyst can for example be that used for obtaining HFC 125 with the processes of the prior art, for example by fluorinating with HF perchloroethylene (WO 95/16654) or by dismutation of HCFC 124 (U.S. Pat. No. 5,345,014).

It is possible to directly carry out the process according to the present invention in the same reactor used for obtaining HCFC 124, with evident economic advantage.

The contact time with the catalyst, measured as the ratio between the catalyst volume and that of the gas flow at the working temperature and pressure, is in the range 1–30 seconds, preferably 5–20 seconds.

The working pressure is not critical, but preferably one operates in the range 1–10 bar.

The reaction is carried out by flowing the CFC 115/HFC 125 mixture, optionally diluted with an inert gas, through the catalyst in a fixed or fluidized bed. When the catalyst is in a fluidized bed the catalyst particles have sizes suitable for this process.

The fluorination catalyst is preferably a chromium salt.

Preferably the catalyst support is aluminum fluoride $AlF_3$ obtainable by alumina fluorination and having a fluorine content not lower than 90%, preferably not lower than 95%, with respect to the stoichiometric.

Generally the used aluminum fluoride is mainly constituted by gamma phase, as described in FR 1,383,927, and has a surface area generally in the range 25–35 $m^2/g$. When the catalyst is used in a fluided bed, the support must have the granulometry suitable for this kind of reactor, as it is well known to the skilled in the prior art.

The chromium amount in the supported catalyst is in the range 5–15% by weight, preferably 10–15%, determined as metal amount with respect to the weight of the finished supported catalyst.

The supported catalyst is preferably prepared by impregnation of the support with an aqueous solution of a soluble chromium salt.

The impregnation of the support can be carried out by any method known in the prior art, for example by the method known as "dry impregnation".

According to this method, the impregnation is carried out by pouring on the support, in sequence, aliquots of an impregnating solution, such that the total volume is not higher than the volume of the aluminum fluoride pores. The solution for the impregnation is prepared by dissolving in water the required amounts of the corresponding salts, preferably chlorides, of the trivalent chromium. The solution is poured in aliquots on the support, drying at 110° C. for some hours after each addition, to evaporate water from the support pores.

The unsupported catalyst is prepared by methods known in the art, for example by precipitation of a soluble trivalent chromium salt as described in U.S. Pat. No. 5,345,014.

Before use the catalyst is activated by calcining for 4–8 hours in a current of inert gas, at the temperature of about 400° C., and then treating it at 360° C. with anhydrous HF for a time comprised between 12 and 24 hours. The operation can be carried out in the reactor used for the purification of HFC 125.

With the process of the invention the purification of HFC 125 can be carried out until the desired extent of the residual amount of CFC 115 combining the reaction temperature, the contact time and optionally the recycle of the product, since in the reaction according to the invention the HFC 125 degradation is negligible, practically the HFC 125 recovery obtained with the process of the invention is substantially quantitative.

During the use the catalyst undergoes a slow deactivation, due to the deposit of organic substance; it can be regenerated by treating it with air at a temperature in the range 300° C.–400° C. for 4–8 hours and then with anhydrous HF at 360° C. for 12–24 hours.

The molar ratio between CFC 115 and HFC 125 in the feeding gaseous mixture is not critical; for example it can range from 0.1 to 4%.

The process of the present invention results advantageous from the industrial point of view since it is sufficient to allow to flow the 125 to be purified on a catalyst bed at the mentioned temperatures without adding any other reactant, in particular without using HF. This greatly simplifies the construction and the handling of the plant, being missing the HF feeding and separation sections, which as well known are the most critical ones. Besides, surprisingly, by the process of the invention, only industrially useful products are obtained and the presence of unsable by-products is negligible.

Some examples are given for illustrative and not limitative purposes of the use possibilities of the invention.

EXAMPLE 1

150 g (120 ml) of supported catalyst, containing 10% by weight of chromium on aluminum fluoride support having a granulometry suitable for the use in a fluidized bed, are introduced in an Inconel® 600 reactor having a 50 mm diameter, with a porous septum at its base and electrically heated, wherein the preheated and premixed reactants are introduced from the bottom. The catalyst is activated by treatment with nitrogen and then with anhydrous HF, as above described. Subsequently the reactor temperature is brought to 320° C. At the pressure of 1 atm, 1.70 moles/h of a CFC 115/HFC 125 mixture containing about 0.15% by moles of CFC 115 are fed. The contact time is 5.2 seconds. The gases outflowing from the reactor are washed in water to absorb acidity traces and analyzed by a gaschromatograph with thermoconductivity detector, equipped with a column formed by perfluoroethers on inert support (Fluorcol® or equivalent). The results of the gaschromatographic analysis on the product mixture are reported hereinafter. The results are expressed in % by moles:

FC 116:0.07
HFC 125:99.78
CFC 115:0.08
HCFC 124:0.07
others: lower than 0.01%

The conversion of CFC 115 is 45%. In the reaction equimolecular amounts of CFC 116 and HCFC 124 are formed.

EXAMPLE 2

Under the conditions described in Example 1, a catalyst amount of 600 g (480 ml) is used and feeding and the reaction temperature (320° C.) are the same as in Example 1, the contact time is 21 seconds. The gases outflowing from the reactor are treated and analyzed as indicated in Example 1. The results are reported hereinafter (% by moles):
FC 116:0.123
HFC 125:99.728
CFC 115:0.054
HCFC 124:0.095
others: lower than 0.01%

The conversion of CFC 115 is 65%.

EXAMPLE 3

In a tubular Inconel® reactor having a 7 mm diameter, 14 g (about 11 ml) of catalyst are introduced. After activation by nitrogen and HF, as above described, the catalyst is heated up to the temperature of 350° C. and 4.6 ml/min, equal to 11.5 mmoles/hour, of HFC 125 containing 0.15% by moles of CFC 115 are fed, diluting the mixture by a helium amount equal to 10 ml/min, thus obtaining a contact time of 21 seconds. The gases outflowing from the reactor are treated and analyzed as indicated in Example 1. The results are reported hereinafter (% by moles):
FC 116:0.243
HFC 125:99.61
CFC 115 0.012
HCFC 124:0.135
others: lower than 0.01%

The conversion of CFC 115 is equal to 92%. As it can be seen, by operating at high temperature and with a sufficiently long contact time, the absence of CFC 115 is almost complete already after only one step.

EXAMPLE 4

The reactor of Example 1 is used with 163 g (120 ml) of catalyst formed by chromium oxide in pellets having a ⅛' cylindrical shape (Engelhard® E-410T). In the reactor HFC 125 containing 0.15% by moles of CFC 115 is fed at a flow of 0.425 moles/hour. The reaction temperature is 320° C. and the contact time is 20 seconds. The gases outflowing from the reactor are treated and analyzed as indicated in Example 1. The results are reported hereinafter (% by moles):
FC 116:0.151
HFC 125: complement to 100
CFC 115:0.016
HCFC 124: 0.145
others: lower than 0.01%

The CFC 115 conversion is 89%.

EXAMPLE 5

Proof that the absence of CFC 115 is not due to the dismutation reaction known in the prior art, but to the reaction between HFC 125 and CFC 115 according to the present invention.

The two following experiments have been carried out.

In the former experiment (experiment 5A) the same catalyst and the same conditions of Example 1 are used, and 1.74 moles/h of a CFC 115/HFC 125 mixture containing 2.5% of CFC 115 are fed. The gases outflowing from the reactor are treated and analyzed as indicated in Example 1. The results are in % by moles, referred to the organic fraction only and are reported hereinafter:

FC 116:0.47
HFC 125:96.99
CFC 115:2.07
HFC 124:0.47

In the latter experiment (experiment 5B, comparative), under the same conditions used above, 1.74 moles/hour of a nitrogen/CFC 115 mixture containing 2.35% of CFC 115, are fed. The gases outflowing from the reactor are treated and analyzed as above. The obtained results, referred to the organic fraction only, are the following:

FC 116:5.3
HFC 125: lower than 0.01
CFC 115:90.4
HFC 124: lower than 0.01
CFC 114:3.6 (isomers $C_2F_4Cl_2$)
CFC 113:0.6 (isomers $C_2F_3Cl_3$) others: 0.1

From the results it ensues that the conversion of CFC 115 in experiment A is 18% and in experiment B is 9.5%. That is to say, in absence of HFC 125, the fed CFC 115 being equal, the conversion of CFC 115 decreases of 50%. Furthermore the mixture of the products obtained in B contains various CFCs which have no industrial use since, as it is well known, they have been banned by the Montreal Treaty.

What is claimed is:

1. A gaseous purification process for pentafluoroethane (HFC 125) from chloropentafluoroethane (CFC 115) impurity, characterized in that pentafluoroethane is allowed to flow on a fluorination catalyst in solid phase, optionally supported, at temperatures in the range 200° C.–400° C.

2. A process according to claim 1, wherein the contact time with the catalyst, measured as the ratio between the catalyst volume and that of the gas flow at the working temperature and pressure, is in the range 1–30 seconds, preferably 5–20 seconds.

3. A process according to claim 1, wherein the working pressure is in the range 1–10 bar.

4. A process according to claim 1, wherein the reaction is carried out by flowing the CFC 115/HFC 125 mixture, optionally diluted with an inert gas, through the catalyst in a fixed or fluidized bed.

5. A process according to claim 1, wherein the fluorination catalyst is a chromium salt.

6. A process according to claim 1, wherein the catalyst support is aluminum fluoride obtainable by alumina fluorination and having a fluorine content not lower than 90%, preferably not lower than 95%, with respect to the stoichiometric.

7. A process according to claim 6, wherein the aluminum fluoride is mainly constituted by gamma phase and has a surface area in the range 25–35 $m^2/g$.

8. A process according to claim 5, wherein in the supported catalyst the chromium amount is in the range 5–15% by weight, preferably 10–15%, determined as metal amount with respect to the weight of the supported catalyst.

9. A process according to claim 1, wherein the molar ratio between CFC 115 and HFC 125 in the feeding gaseous mixture ranges from 0.1 to 4%.

* * * * *